US00PP36172P3

(12) United States Plant Patent
Bergman

(10) Patent No.: US PP36,172 P3
(45) Date of Patent: Oct. 1, 2024

(54) ***LANTANA* PLANT NAMED 'LANZ0046'**

(50) Latin Name: ***Lantana camara* L.**
Varietal Denomination: LANZ0046

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/876,748

(22) Filed: Jul. 29, 2022

(65) Prior Publication Data

US 2024/0099170 P1 Mar. 21, 2024

(30) Foreign Application Priority Data

Jul. 27, 2022 (QZ) ..... PBR 2022/1785

(51) Int. Cl.

| | |
|---|---|
| ***A01H 5/02*** | (2018.01) |
| ***A01H 6/00*** | (2018.01) |
| ***A01H 6/86*** | (2018.01) |

(52) U.S. Cl.
USPC ..... Plt./227
CPC ..... *A01H 6/86* (2018.05); *A01H 6/00* (2018.05)

(58) Field of Classification Search
USPC ..... Plt./227
CPC ..... A01H 6/86; A01H 5/02; A01H 5/00
See application file for complete search history.

(56) References Cited

PUBLICATIONS

CPVO Application Consultation Version 4.12.6 for 'LANZ0046'; Nov. 3, 2023; 3 pages.*

* cited by examiner

*Primary Examiner* — Kent L Bell
(74) *Attorney, Agent, or Firm* — Dale Skalla

(57) ABSTRACT

A new *Lantana* plant named 'LANZ0046' having large white umbels, newly opened flowers are white with a yellow throat, mature flowers are white, excellent flower production, large plant growth and uniform dense semi-spreading habit with medium-small sized dark green foliage.

1 Drawing Sheet

Figure 1:
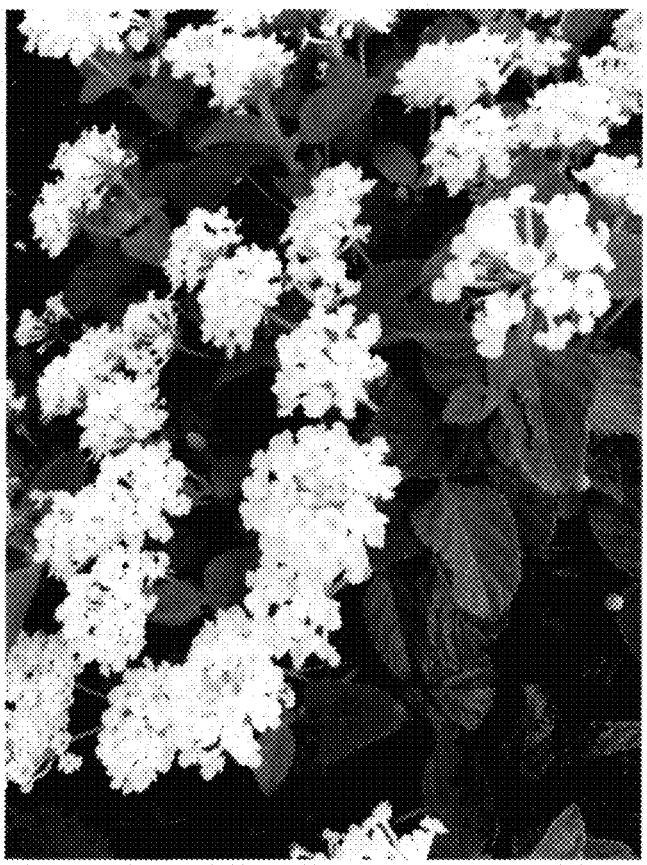

Latin name of the genus and species of the plant claimed: *Lantana camara* L.

Varietal denomination: 'LANZ0046'.

BACKGROUND OF THE NEW PLANT

The present invention comprises a new *Lantana*, botanically known as *Lantana camara*L., and hereinafter referred to by the variety name 'LANZ0046'.

'LANZ0046' is a product of a planned breeding program in Gilroy, California. The new cultivar 'LANZ0046' has large white umbels, newly opened flowers are white with a yellow throat, mature flowers are white, excellent flower production, large plant growth and uniform dense semi-spreading habit with medium-small sized dark green foliage.

The new *Lantana* cultivar, 'LANZ0046', is the result of cross-pollination made in Gilroy, California in the summer of 2017. The female parent of the new cultivar is the proprietary *Lantana camara* breeding selection 'I0043-1', not patented, characterized by its white inflorescences, medium green-colored foliage and compact rounded growth habit. 'LANZ0046' differs from 'I0043-1' by having a smaller yellow throat, darker green foliage, and much larger plant size. The male parent of the new cultivar is 'Balucwhit', U.S. Pat. No. 16,523, having smaller white flowers, an overall larger plant size and a less uniform plant habit than 'LANZ0046'.

The resulting seed was sown in March 2018 in a controlled greenhouse environment in Gilroy, California, and 'LANZ0046' was selected as one flowering plant within the progeny of the stated cross in June of 2018.

The first act of asexual reproduction of 'LANZ0046' was accomplished when vegetative stem cuttings were propagated from the initial selection in August 2018, in Gilroy, California.

BRIEF SUMMARY OF INVENTION

Horticultural examination of plants grown from cuttings of the plant initiated in August 2018, in Gilroy, California, and continuing thereafter, has demonstrated that the combination of characteristics as herein disclosed for 'LANZ0046' are firmly fixed and are retained through successive generations of asexual reproduction.

'LANZ0046' has not been observed under all possible environmental conditions. The phenotype may vary significantly with variations in environment such as temperature, light intensity, and day length.

A Plant Breeder's Right for this cultivar was applied for in the European Union on Jul. 27, 2022, No. 2022/1785. 'LANZ0046' has not been made publicly available prior to the effective filing date of this application, notwithstanding any disclosure that may have been made less than one year prior to the effective filing date of this application by the inventor or another who obtained 'LANZ0046' directly from the inventor.

The following traits have been repeatedly observed and are determined to be basic characteristics of the new variety.

The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0046' with colors being as true as possible with an illustration of this type.

Figure 2:
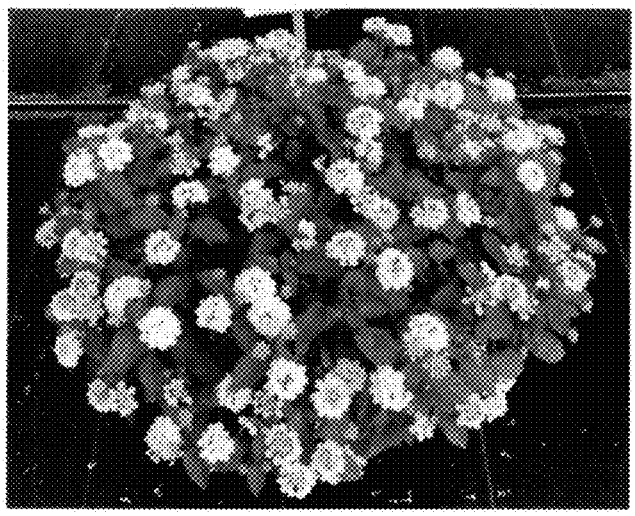

The photographic drawings show in FIG. 1 a close view of inflorescences taken in Vero Beach, Florida in September in 2021, and in FIG. 2 a whole flowering plant, approximately 2 months of age, taken in Gilroy, California in August 2020.

DETAILED BOTANICAL DESCRIPTION

The plant descriptions and measurements were taken in Gilroy, California in July 2022. The plants were approximately 3.5 months old and were growing in 14 inch pots, three plants per pot, in a greenhouse.

Color references are made to The Royal Horticultural Society Colour Chart (R.H.S.) 2001.

TABLE 1

DIFFERENCES BETWEEN THE NEW VARIETY 'LANZ0046' AND A MOST SIMILAR VARIETY

| Traits | 'LANZ0046' | 'Ban Whit', U.S. Plant Pat. No. PP21,590 |
|---|---|---|
| Seed set: | Low seed set | Moderate seed set |
| Flower color: | White with small yellow eye | White with large yellow eye |
| Plant size: | Larger growing | Smaller growing |

Plant:

*Form, growth and habit.*—Semi-woody, grown as an annual or perennial; vigorous semi-spreading habit; very well branched.

*Plant height.*—20 cm.

*Plant height (inflorescence included).*—22 cm.

*Plant width.*—42 cm.

Foliage:

*Type.*—Opposite.

*Immature, leaf color, upper surface.*—Closest to RHS 137A.

*Lower surface.*—Closest to RHS 137C.

*Mature, leaf color, upper surface.*—RHS 139A.

*Lower surface.*—Closest to RHS 137B.

*Length.*—5.2-6.0 cm.

*Width.*—3.6-4.1 cm.

*Shape.*—Ovate.

*Base shape.*—Rounded and slightly inequilateral.

*Apex shape.*—Acute.

*Margin.*—Serrate.

*Texture, upper surface.*—Hairy.

*Texture, lower surface.*—Hairy.

*Pattern of veining.*—Pinnate.

*Petioles color.*—RHS 137C.

*Petioles length.*—1.4-1.8 cm.

*Diameter of petiole.*—01.5 cm.

*Texture (upper and lower surface).*—Very short hairs.

Stem:

*Color of stem.*—RHS 146D.

*Length of stem.*—20.0 cm.

*Diameter.*—0.3 cm.

*Length of internodes.*—2.5-4.5 cm.

*Texture.*—Some hairs.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 36.

*Quantity of inflorescences per plant.*—About 20.

*Lastingness of individual blooms on the plant.*—About 3 weeks (depending on temperatures).

*Fragrance.*—Slightly spicy.

*Umbel horizontal diameter.*—4.2-4.4 cm.

*Umbel vertical height.*—1.8-2.1 cm.

*Peduncle color.*—RHS 138A.

*Length of peduncle.*—5.0-6.3 cm.

*Peduncle diameter.*—0.2 cm.

*Texture.*—Some hairs.

Flower:

*Floret form.*—Corolla salver-shaped to shallow cup-shaped, with a relatively long tube at the base; each flower subtended by a single bract.

*Length of floret.*—2.0 cm.

*Width of floret.*—1.2 cm.

*Depth of floret.*—1.0 cm.

*Young floret, color upper surface.*—RHS 155A with RHS 6B surrounding throat.

*Young floret, color lower surface.*—RHS 155A.

*Mid age floret, color upper surface.*—RHS 155D.

*Mid age floret, color lower surface.*—RHS 155D.

*Mature florets, color upper surface.*—RHS 155D.

*Mature floret, color lower surface.*—RHS 155D.

*Apex shape.*—Rounded.

*Degree of lobation.*—Moderate.

*Margin.*—Entire.

*Base.*—Fused.

*Texture, upper surface.*—Smooth.

*Lower surface.*—Smooth.

*Tube, color outer surface.*—RHS 155D.

*Tube, color inner surface.*—RHS 155D.

*Tube, length.*—1.3 cm.

*Tube, diameter (at opening).*—0.15 cm.

*Tube, texture outer surface.*—Smooth.

*Inner surface.*—Very small hairs.

Bud (just before opening):

*Color.*—RHS 4D.

*Length.*—1.0 cm.

*Width.*—0.3 cm at the apex.

*Shape.*—Tubular with a flared apex.

Bract:

*Color upper and lower surface.*—Closest to RHS 138A.

*Shape.*—Linear.

*Apex.*—Acute.

*Base.*—Linear, stipulate.

*Margin.*—Entire.

*Length.*—0.60-0.8 cm.

*Diameter.*—0.15 cm.

*Texture, upper surface.*—Small hairs.

*Lower surface.*—Small hairs.

Calyx:

*Number of sepals.*—5, fused sepals forming a short tube around the base of the floret.

*Sepal shape.*—Tubular.

*Color of sepals, upper and lower surfaces*.—RHS 147D.
*Length of sepals*.—0.20 cm.
*Width of sepals*.—0.15 cm.
*Apex shape*.—Obtuse.
*Apex margins*.—Entire.
*Texture, outer surface*.—Small hairs.
*Inner surface*.—Smooth.

Reproductive organs:
*Gynoecium*.—
*Pistil quantity*.—One.
*Length*.—0.4 cm.
*Style color*.—RHS 150D.
*Style length*.—0.25 cm.
*Stigma color*.—RHS 144A.
*Ovary color*.—RHS 146B.
*Ovary length*.—0.1 cm.
*Ovary diameter*.—0.1 cm.
*Androecium*.—
*Stamen quantity*.—4.
*Color of filaments*.—RHS 159D.
*Length filaments*.—0.05 cm.
*Anther color*.—RHS 4C.
*Length of anthers*.—0.1 cm.
*Color of pollen*.—RHS 4D.
*Pollen amount*.—Scant.
*Fertility/seed set*.—Low.
*Disease/pest resistance*.—No significant disease or pest issues have been identified or observed.

What is claimed is:

1. A new and distinct variety of *Lantana* plant named 'LANZ0046' substantially as illustrated and described herein.

* * * * *